United States Patent
Krijgsveld et al.

(10) Patent No.: US 6,838,435 B1
(45) Date of Patent: Jan. 4, 2005

(54) ISOLATED AND RECOMBINANT ANTIMICROBIAL PEPTIDES THROMBOCIDIN-1 (TC-1) AND THROMBOCIDIN-2(TC-2) OR VARIANTS THEREOF

(75) Inventors: Jeroen Krijgsveld, Amsterdam (NL); Sebastianus Antonius Johannes Zaat, Amstelveen (NL); Jacob Dankert, Baambrugge (NL); Alma Johanna Kuijpers, Enschede (NL); Gerardus Henricus Maria Engbers, Oldenzaal (NL); Jan Feijen, Hengelo (NL)

(73) Assignees: Academisch Ziekenhuis bij de Universiteit van Amsterdam (NL); Universiteit Twente (NL); Nederlandse Organisatie Voor Wetenschappelijk Onderzoek (NL)

( * ) Notice: Subject to any disclaimer, the term of this patent is extended or adjusted under 35 U.S.C. 154(b) by 0 days.

(21) Appl. No.: 09/509,391

(22) PCT Filed: Sep. 25, 1998

(86) PCT No.: PCT/EP98/06183

§ 371 (c)(1), (2), (4) Date: Jul. 7, 2000

(87) PCT Pub. No.: WO99/15548

PCT Pub. Date: Apr. 1, 1999

(30) Foreign Application Priority Data

Sep. 25, 1997 (EP) .............................. 97202934
May 1, 1998 (EP) .............................. 98201411

(51) Int. Cl.[7] .............................. A61K 38/00

(52) U.S. Cl. .............................. 514/9

(58) Field of Search .............................. 514/2, 9, 12; 536/300, 536/350; 530/300

(56) References Cited

U.S. PATENT DOCUMENTS

| | | | | |
|---|---|---|---|---|
| 4,725,576 A | * | 2/1988 | Pollock et al. | ................ 424/54 |
| 5,073,627 A | * | 12/1991 | Curtis et al. | ............... 435/69.5 |
| 5,656,724 A | * | 8/1997 | Daly et al. | ................ 424/85.2 |

FOREIGN PATENT DOCUMENTS

| | | | | |
|---|---|---|---|---|
| WO | WO 90/06321 | * | 6/1990 | |
| WO | 9006321 | | 6/1990 | ............ C07K/7/10 |
| WO | 9719173 | | 5/1997 | ........... C12N/15/19 |

OTHER PUBLICATIONS

Cimbollek M, Nies B, Wenz R, Kreuter J. Antibiotic–impregnated heart valve sewing rings for treatment and prophylaxis of bacterial endocarditis. Antimicrob Agents Chemother. Jun. 1996;40(6):1432–7.*

Harwig et al.; "Intramolecular disulfide bonds enhance the antimicrobial and lytic activities of protegrins at physiological sodium chloride concentrations", *Eur. J. Biochem.* 240, pp. 352–357 (1996).

Lindley et al.; "Synthesis and expression in *Escherichia coli* of the gene encoding monocyte–derived neutrophil–activating factor: Biological equivalence between natural and recombinant neutrophil–activating factor"; *Proc. Natl. Acad. Sci. USA*, vol. 85, pp. 9199–9203 (Dec. 1988).

Piers et al.; "Recombinant DNA procedures for producing small antimicrobial cationic peptides in bacteria"; *Gene.* 134, pp. 7–13 (1993).

Proudfoot et al.; "Structure and Bioactivity of Recombinant Human CTAP–III and NAP–2"; *Journal of Protein Chemistry*, vol. 16, No. 1, pp. 37–49 (1997).

Selsted et al.; "Determination of the Disulfide Array in the Human Defensin HNP–2" (A Covalently Cyclized Peptide); *Journal of Biological Chemistry*, vol. 264,No. 7, Mar. 5 Issue, pp. 4003–4007 (1989).

Yomogida et al.; "Involvement of Cysteine Residues in the Biological Activity of the Active Fragments of Guinea Pig Neutrophil Cationic Peptides"; *Infection and Immunity*, vol. 63, No. 6, pp. 2344–2346 (Jun. 1995); Amer. Society for Microbiology (1995).

Yeaman et al., Platelet Microbicidal Protein Alone and in Combination with Antibiotics Reduces *Staphylococcus aureus* Adherence to Platelets in Vitro, Aug. 1994, pp. 3416–3423.

Yeaman et al., Partial Characterization and Staphylocidal Activity of Thrombin–Induced Platelet Microbicidal Protein, Mar. 1992, pp. 1202–1209.

(List continued on next page.)

Primary Examiner—Karen Cochrane Carlson
Assistant Examiner—Sheridan K Snedden
(74) Attorney, Agent, or Firm—Webb Ziesenheim Logsdon Orkin & Hanson, P.C.

(57) ABSTRACT

The present invention relates to isolated and recombinant antimicrobial peptides thrombocidin-1 (TC-1) and thrombocidin-2 (TC-2), or variants thereof, which comprise at least in part the sequence as shown in FIG. 1 indicated by the label TC-1 and TC-2, and have antimicrobial activity against gram-positive and gram-negative bacteria, for example *Escherichia coli, Bacillus subtilis, Streptococcus sanguis, Streptococcus pneumoniae, Staphylococcus epidermis,* and *Staphylococcus aureus*, and/or against fungi, for example *Candida albicans, C. glabarata, Cryptococcus neoformans, Aspergillus flavus, A. fumigatus,* and *Pseudoalleschenia* spec. The invention further relates to the use of said peptides, or variants thereof, for the preparation of a medicament for the treatment of bacterial or fungal infections, such as endocarditis, in humans and animals and the use of said peptides, or variants thereof, in release systems for prevention of bacterial or fungal infections in humans and animals.

8 Claims, 14 Drawing Sheets

OTHER PUBLICATIONS

Figure 3:
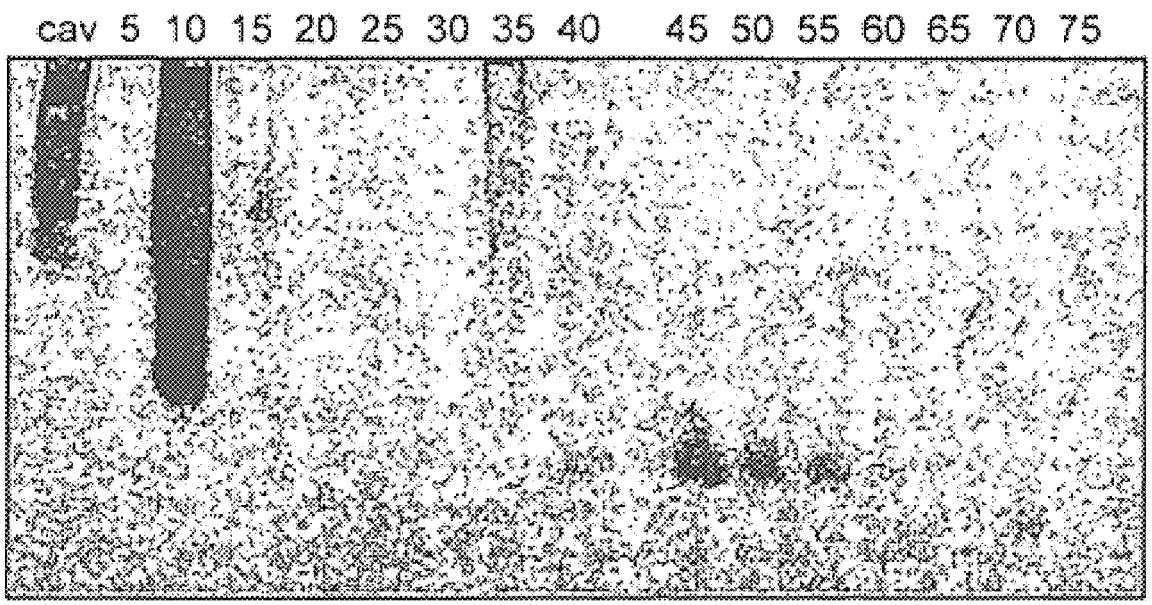

Dankert et al., Involvement of Bactericidal Factors from Thrombin–Stimulated Platelets in Clearance of Adherent Viridans Streptococci in Experimental Infective Endocarditis, Feb. 1995, pp. 663–671.

Zaat et al., Cell–Adherent Glucan Does Not Protect Endocarditis–Causing Viridans Streptococci Against Bactericidal Proteins from Human Blood Platelets, 1997, pp. 709–712.

Standiford et al., Role of Chemokines in Antibacterial Host Defense, 1997, pp. 220–241.

Harwig et al., Purification of Cysteine–Rich Bioactive Peptides from Leukocytes by Continuous Acid–Urea–Polyacrylamide Gel Electrophoresis, Feb. 1993, pp. 382–386.

Yeaman et al., Fluconazole and platelet microbicidal protein inhibit Candida adherence to platelets in vitro, Jul. 1997, p. 1.

Yeaman et al., Thrombin–induced rabbit platelet microbicidal protein in fungicidal in vitro, Mar. 1993, p. 1.

* cited by examiner

```
IC-1:                                  LRC MCIKT TSGIH PKNIQ SLEVI GKGTH CNQVE VIATL KDGRK ICLDP DAPRI KKIVQ KKLAG DESAD
                                                                                                               (SEQ ID NO: 12)
IC-1α:                           AELRC MCIKT TSGIH PKNIQ SLEVI GKGTH CNQVE VIATL KDGRK ICLDP DAPRI KKIVQ KKLAG DES
                                                                                                               (SEQ ID NO: 3)
IC-2:        NLAKG KEESL DSDLY AELRC MCIKT TSGIH PKNIQ SLEVI GKGTH CNQVE VIATL KDGRK ICLDP DAPRI KKIVQ KKLAG DES
                                                                                                               (SEQ ID NO: 6)
CTAP-III:    NLAKG KEESL DSDLY AELRC MCIKT TSGIH PKNIQ SLEVI GKGTH CNQVE VIATL KDGRK ICLDP DAPRI KKIVQ KKLAG DESAD
                                                                                                               (SEQ ID NO: 1)
NAP-2:                           AELRC MCIKT TSGIH PKNIQ SLEVI GKGTH CNQVE VIATL KDGRK ICLDP DAPRI KKIVQ KKLAG DESAD
                                                                                                               (SEQ ID NO: 13)
```

FIG. 1

```
rMTC-1:   MAELRC MCIKT TSGIH PKNIQ SLEVI GKGTH CNQVE VIATL KDGRK ICLDP DAPRI KKIVQ KKLAG DES
                                                                                        (SEQ ID NO: 14)
rMTC-2:   MNLAKGKEESLDSDLYAELRC MCIKT TSGIH PKNIQ SLEVI GKGTH CNQVE VIATL KDGRK ICLDP DAPRI KKIVQ KKLAG DES
                                                                                        (SEQ ID NO: 15)
rYTC-1:   MGHHHHHHHHHSSGHIEGR M YLRCMCIKT TSGIH PKNIQ SLEVI GKGTH CNQVE VIATL KDGRK ICLDP DAPRI KKIVQ KKLAG DESAD
                                                                                        (SEQ ID NO: 16)
rYNAP:    MGHHHHHHHHHSSGHIEGR M YAELRCMCIKT TSGIH PKNIQ SLEVI GKGTH CNQVE VIATL KDGRK ICLDP DAPRI KKIVQ KKLAG DESAD
                                                                                        (SEQ ID NO: 17)
rMCTAP:   MNLAKGKEESLDSDLYAELRC MCIKT TSGIH PKNIQ SLEVI GKGTH CNQVE VIATL KDGRK ICLDP DAPRI KKIVQ KKLAG DESAD
                                                                                        (SEQ ID NO: 18)
```

FIG. 2

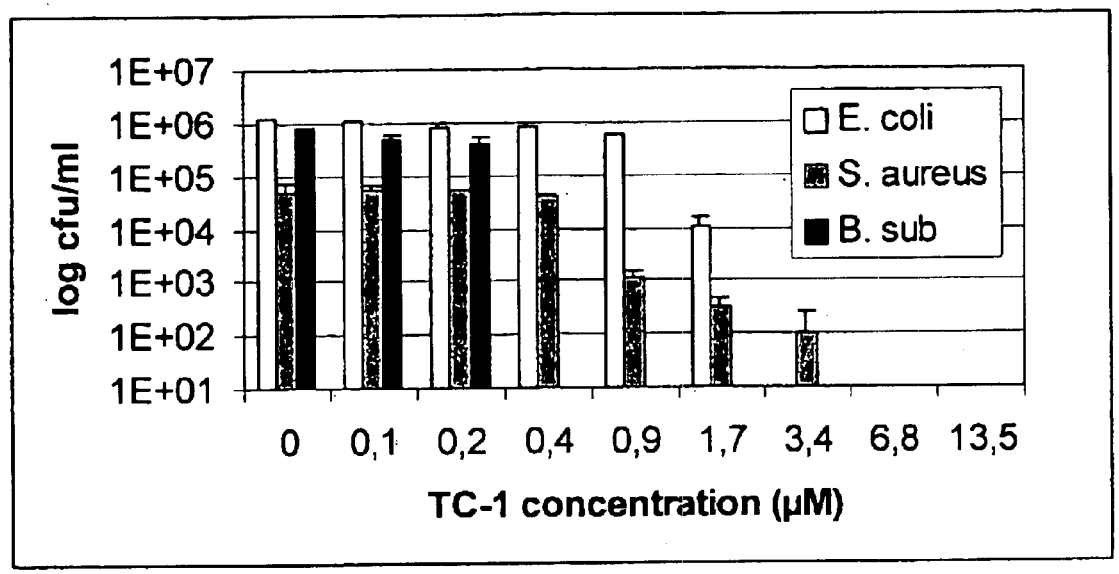
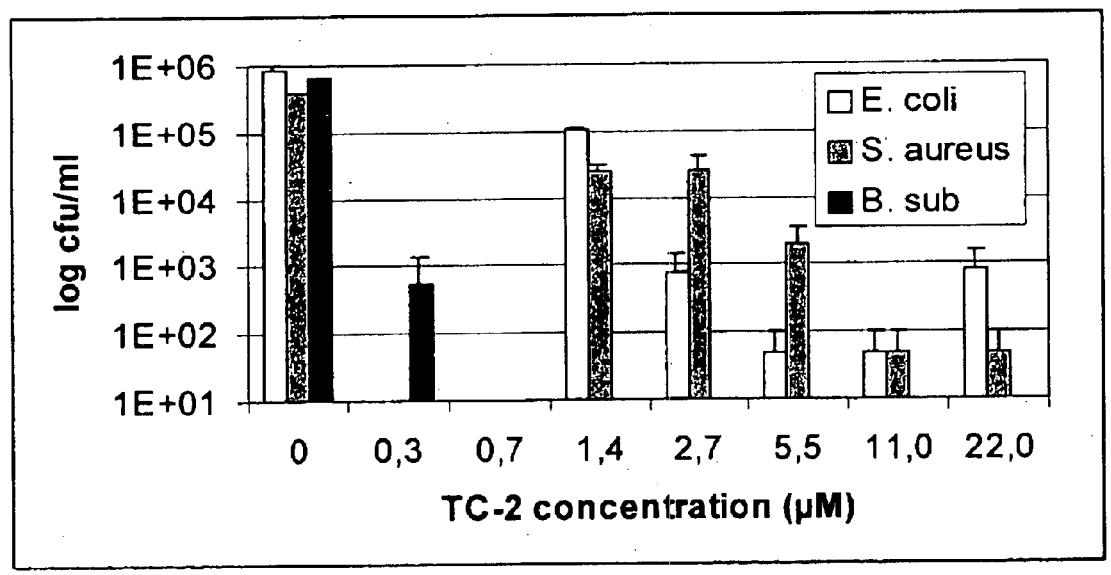
FIG. 10

SEQUENCE LISTING

```
<160> NUMBER OF SEQ ID NOS: 18

<210> SEQ ID NO 1
<211> LENGTH: 85
<212> TYPE: PRT
<213> ORGANISM: Homo sapiens
<220> FEATURE:
<223> OTHER INFORMATION: CTAP-III (connective tissue activating peptide)

<400> SEQUENCE: 1

Asn Leu Ala Lys Gly Lys Glu Glu Ser Leu Asp Ser Asp Leu Tyr Ala
 1               5                  10                  15

Glu Leu Arg Cys Met Cys Ile Lys Thr Thr Ser Gly Ile His Pro Lys
            20                  25                  30

Asn Ile Gln Ser Leu Glu Val Ile Gly Lys Gly Thr His Cys Asn Gln
        35                  40                  45

Val Glu Val Ile Ala Thr Leu Lys Asp Gly Arg Lys Ile Cys Leu Asp
    50                  55                  60

Pro Asp Ala Pro Arg Ile Lys Lys Ile Val Gln Lys Lys Leu Ala Gly
65                  70                  75                  80

Asp Glu Ser Ala Asp
                85
```

```
<210> SEQ ID NO 2
<211> LENGTH: 4
<212> TYPE: PRT
<213> ORGANISM: Homo sapiens
<220> FEATURE:
<223> OTHER INFORMATION: N-terminus of TC-1a and TC-1b thrombocidins

<400> SEQUENCE: 2

Ala Glu Leu Arg
 1

<210> SEQ ID NO 3
<211> LENGTH: 68
<212> TYPE: PRT
<213> ORGANISM: Homo sapiens
<220> FEATURE:
<223> OTHER INFORMATION: TC-1* thrombocidin variant

<400> SEQUENCE: 3

Ala Glu Leu Arg Cys Met Cys Ile Lys Thr Thr Ser Gly Ile His Pro
 1               5                  10                  15

Lys Asn Ile Gln Ser Leu Glu Val Ile Gly Lys Gly Thr His Cys Asn
            20                  25                  30

Gln Val Glu Val Ile Ala Thr Leu Lys Asp Gly Arg Lys Ile Cys Leu
        35                  40                  45

Asp Pro Asp Ala Pro Arg Ile Lys Lys Ile Val Gln Lys Lys Leu Ala
    50                  55                  60

Gly Asp Glu Ser
 65

<210> SEQ ID NO 4
<211> LENGTH: 5
<212> TYPE: PRT
<213> ORGANISM: Homo sapiens
<220> FEATURE:
<223> OTHER INFORMATION: N-terminus of TC-1d thrombocidin

<400> SEQUENCE: 4

Tyr Ala Glu Leu Arg
 1               5

<210> SEQ ID NO 5
<211> LENGTH: 5
<212> TYPE: PRT
<213> ORGANISM: Homo sapiens
<220> FEATURE:
<223> OTHER INFORMATION: C-terminus of TC-1d thrombocidin

<400> SEQUENCE: 5

Ala Gly Asp Glu Ser
 1               5

<210> SEQ ID NO 6
<211> LENGTH: 83
<212> TYPE: PRT
<213> ORGANISM: Homo sapiens
<220> FEATURE:
<223> OTHER INFORMATION: TC-2 thrombocidin

<400> SEQUENCE: 6

Asn Leu Ala Lys Gly Lys Glu Glu Ser Leu Asp Ser Asp Leu Tyr Ala
 1               5                  10                  15

Glu Leu Arg Cys Met Cys Ile Lys Thr Thr Ser Gly Ile His Pro Lys
            20                  25                  30
```

-continued

```
Asn Ile Gln Ser Leu Glu Val Ile Gly Lys Gly Thr His Cys Asn Gln
         35                  40                  45

Val Glu Val Ile Ala Thr Leu Lys Asp Gly Arg Lys Ile Cys Leu Asp
     50                  55                  60

Pro Asp Ala Pro Arg Ile Lys Lys Ile Val Gln Lys Lys Leu Ala Gly
 65                  70                  75                  80

Asp Glu Ser

<210> SEQ ID NO 7
<211> LENGTH: 34
<212> TYPE: DNA
<213> ORGANISM: Homo sapiens
<220> FEATURE:
<223> OTHER INFORMATION: Forward primer
<220> FEATURE:
<221> NAME/KEY: misc_feature
<222> LOCATION: (5)...(10)
<223> OTHER INFORMATION: BamHI restriction site

<400> SEQUENCE: 7
tataggatcc atgagcctca gacttgatac cacc                          34

<210> SEQ ID NO 8
<211> LENGTH: 38
<212> TYPE: DNA
<213> ORGANISM: Homo sapiens
<220> FEATURE:
<223> OTHER INFORMATION: Reverse primer
<220> FEATURE:
<221> NAME/KEY: misc_feature
<222> LOCATION: (5)...(10)
<223> OTHER INFORMATION: BamHI restriction site
<220> FEATURE:
<221> NAME/KEY: terminator
<222> LOCATION: (11)...(13)
<223> OTHER INFORMATION: Stop sequence

<400> SEQUENCE: 8
tataggatcc tcaatcagca gattcatcac ctgccaat                      38

<210> SEQ ID NO 9
<211> LENGTH: 33
<212> TYPE: DNA
<213> ORGANISM: Homo sapiens
<220> FEATURE:
<223> OTHER INFORMATION: Forward primer for CTAP-III and TC-2
<220> FEATURE:
<221> NAME/KEY: misc_feature
<222> LOCATION: (7)...(12)
<223> OTHER INFORMATION: NdeI restriction site

<400> SEQUENCE: 9
gtgtaacata tgaacttggc gaaaggcaaa gag                           33

<210> SEQ ID NO 10
<211> LENGTH: 33
<212> TYPE: DNA
<213> ORGANISM: Homo sapiens
<220> FEATURE:
<223> OTHER INFORMATION: Forward primer for NAP-2 and TC-1*
<220> FEATURE:
<221> NAME/KEY: misc_feature
<222> LOCATION: (7)...(12)
<223> OTHER INFORMATION: NdeI restriction site

<400> SEQUENCE: 10
gtgtaacata tgtatgctga actccgctgc atg                           33
```

-continued

```
<210> SEQ ID NO 11
<211> LENGTH: 36
<212> TYPE: DNA
<213> ORGANISM: Homo sapiens
<220> FEATURE:
<223> OTHER INFORMATION: Forward primer for TC-1
<220> FEATURE:
<221> NAME/KEY: misc_feature
<222> LOCATION: (7)...(12)
<223> OTHER INFORMATION: NdeI restriction site

<400> SEQUENCE: 11
gtgtaacata tgtatctccg ctgcatgtgt ataaag                                 36

<210> SEQ ID NO 12
<211> LENGTH: 68
<212> TYPE: PRT
<213> ORGANISM: Homo sapiens
<220> FEATURE:
<223> OTHER INFORMATION: TC-1 thrombocidin

<400> SEQUENCE: 12
```

Leu Arg Cys Met Cys Ile Lys Thr Thr Ser Gly Ile His Pro Lys Asn
 1               5                  10                  15

Ile Gln Ser Leu Glu Val Ile Gly Lys Gly Thr His Cys Asn Gln Val
            20                  25                  30

Glu Val Ile Ala Thr Leu Lys Asp Gly Arg Lys Ile Cys Leu Asp Pro
        35                  40                  45

Asp Ala Pro Arg Ile Lys Lys Ile Val Gln Lys Lys Leu Ala Gly Asp
    50                  55                  60

Glu Ser Ala Asp
 65

```
<210> SEQ ID NO 13
<211> LENGTH: 70
<212> TYPE: PRT
<213> ORGANISM: Homo sapiens
<220> FEATURE:
<223> OTHER INFORMATION: NAP-2 (neutrophil activating peptide)

<400> SEQUENCE: 13
```

Ala Glu Leu Arg Cys Met Cys Ile Lys Thr Thr Ser Gly Ile His Pro
 1               5                  10                  15

Lys Asn Ile Gln Ser Leu Glu Val Ile Gly Lys Gly Thr His Cys Asn
            20                  25                  30

Gln Val Glu Val Ile Ala Thr Leu Lys Asp Gly Arg Lys Ile Cys Leu
        35                  40                  45

Asp Pro Asp Ala Pro Arg Ile Lys Lys Ile Val Gln Lys Lys Leu Ala
    50                  55                  60

Gly Asp Glu Ser Ala Asp
 65                  70

```
<210> SEQ ID NO 14
<211> LENGTH: 69
<212> TYPE: PRT
<213> ORGANISM: Escherichia coli
<220> FEATURE:
<223> OTHER INFORMATION: rMTC-1* (TC-1* carrying an additional
      N-terminal methionine)

<400> SEQUENCE: 14
```

Met Ala Glu Leu Arg Cys Met Cys Ile Lys Thr Thr Ser Gly Ile His
 1               5                  10                  15

```
Pro Lys Asn Ile Gln Ser Leu Glu Val Ile Gly Lys Gly Thr His Cys
         20                  25                  30

Asn Gln Val Glu Val Ile Ala Thr Leu Lys Asp Gly Arg Lys Ile Cys
         35                  40                  45

Leu Asp Pro Asp Ala Pro Arg Ile Lys Lys Ile Val Gln Lys Lys Leu
     50                  55                  60

Ala Gly Asp Glu Ser
 65

<210> SEQ ID NO 15
<211> LENGTH: 84
<212> TYPE: PRT
<213> ORGANISM: Escherichia coli
<220> FEATURE:
<223> OTHER INFORMATION: rMTC-2 (TC-2 carrying an additional N-terminal
      methionine)

<400> SEQUENCE: 15

Met Asn Leu Ala Lys Gly Lys Glu Glu Ser Leu Asp Ser Asp Leu Tyr
 1               5                  10                  15

Ala Glu Leu Arg Cys Met Cys Ile Lys Thr Thr Ser Gly Ile His Pro
             20                  25                  30

Lys Asn Ile Gln Ser Leu Glu Val Ile Gly Lys Gly Thr His Cys Asn
         35                  40                  45

Gln Val Glu Val Ile Ala Thr Leu Lys Asp Gly Arg Lys Ile Cys Leu
     50                  55                  60

Asp Pro Asp Ala Pro Arg Ile Lys Lys Ile Val Gln Lys Lys Leu Ala
 65                  70                  75                  80

Gly Asp Glu Ser

<210> SEQ ID NO 16
<211> LENGTH: 91
<212> TYPE: PRT
<213> ORGANISM: Escherichia coli
<220> FEATURE:
<223> OTHER INFORMATION: rYTC-1 (TC-1 with an N-terminal His-tag, plus a
      tyrosine residue)
<220> FEATURE:
<221> NAME/KEY: SITE
<222> LOCATION: (1)...(21)
<223> OTHER INFORMATION: Antimicrobial activity enhancing sequence
      (Histag)

<400> SEQUENCE: 16

Met Gly His His His His His His His His Ser Ser Gly His
 1               5                  10                  15

Ile Glu Gly Arg His Met Tyr Leu Arg Cys Met Cys Ile Lys Thr Thr
             20                  25                  30

Ser Gly Ile His Pro Lys Asn Ile Gln Ser Leu Glu Val Ile Gly Lys
         35                  40                  45

Gly Thr His Cys Asn Gln Val Glu Val Ile Ala Thr Leu Lys Asp Gly
     50                  55                  60

Arg Lys Ile Cys Leu Asp Pro Asp Ala Pro Arg Ile Lys Lys Ile Val
 65                  70                  75                  80

Gln Lys Lys Leu Ala Gly Asp Glu Ser Ala Asp
                 85                  90

<210> SEQ ID NO 17
<211> LENGTH: 93
<212> TYPE: PRT
```

```
<213> ORGANISM: Escherichia coli
<220> FEATURE:
<223> OTHER INFORMATION: rYNAP (NAP with an N-terminal His-tag, plus a
      tyrosine residue)
<220> FEATURE:
<221> NAME/KEY: SITE
<222> LOCATION: (1)...(21)
<223> OTHER INFORMATION: Antimicrobial activity enhancing sequence
      (Histag)

<400> SEQUENCE: 17

Met Gly His His His His His His His His His Ser Ser Gly His
 1               5                  10                  15

Ile Glu Gly Arg His Met Tyr Ala Glu Leu Arg Cys Met Cys Ile Lys
            20                  25                  30

Thr Thr Ser Gly Ile His Pro Lys Asn Ile Gln Ser Leu Glu Val Ile
        35                  40                  45

Gly Lys Gly Thr His Cys Asn Gln Val Glu Val Ile Ala Thr Leu Lys
        50                  55                  60

Asp Gly Arg Lys Ile Cys Leu Asp Pro Asp Ala Pro Arg Ile Lys Lys
65                  70                  75                  80

Ile Val Gln Lys Lys Leu Ala Gly Asp Glu Ser Ala Ile
                85                  90

<210> SEQ ID NO 18
<211> LENGTH: 86
<212> TYPE: PRT
<213> ORGANISM: Escherichia coli
<220> FEATURE:
<223> OTHER INFORMATION: rMCTAP (CTAP with an additional N-terminal
      methionine)

<400> SEQUENCE: 18

Met Asn Leu Ala Lys Gly Lys Glu Glu Ser Leu Asp Ser Asp Leu Tyr
 1               5                  10                  15

Ala Glu Leu Arg Cys Met Cys Ile Lys Thr Thr Ser Gly Ile His Pro
            20                  25                  30

Lys Asn Ile Gln Ser Leu Glu Val Ile Gly Lys Gly Thr His Cys Asn
        35                  40                  45

Gln Val Glu Val Ile Ala Thr Leu Lys Asp Gly Arg Lys Ile Cys Leu
        50                  55                  60

Asp Pro Asp Ala Pro Arg Ile Lys Lys Ile Val Gln Lys Lys Leu Ala
65                  70                  75                  80

Gly Asp Glu Ser Ala Asp
                85
```

US 6,838,435 B1

ISOLATED AND RECOMBINANT ANTIMICROBIAL PEPTIDES THROMBOCIDIN-1 (TC-1) AND THROMBOCIDIN-2(TC-2) OR VARIANTS THEREOF

The present invention relates to isolated antimicrobial peptides TC-1 and TC-2 or variants thereof and to recombinantly prepared TC-1 and TC-2 or variants thereof.

Antibiotics are commonly used in the treatment and/or prevention of infectious diseases caused by various microorganisms. However, resistance of bacteria against these antibiotics often occurs. Thus, methicillin-resistant *Staphylococcus aureus* (MRSA) and methicillin-resistant *Staphylococcus epidermis* (MRSE) are well-known resistant microorganisms, among other bacterial species, responsible for serious nosocomial infections that are very difficult to treat.

Conventional antibiotics kill bacteria by binding to specific targets that are involved in bacterial DNA and protein synthesis or in cell wand synthesis. Resistance can occur when bacteria modify these targets, such that antibiotics do not bind to these proteins, or when bacteria produce specific enzymes that inactivate the antibiotics. Glycopeptide antibiotics such as vancomycin can be used to treat these resistant microorganisms, but their use must be limited to prevent development of resistance to these "kill or cure" remedies as well.

As more and more bacteria become resistant to routinely applied antibiotics, there is an increasingly urgent need for alternative antibacterial agents.

The object of the present invention is therefore to provide new antimicrobial agents against which microorganisms do not rapidly become resistant.

This object is achieved by the invention by providing new, isolated or recombinant, antimicrobial peptides thrombocidin-1 (TC-1) (SEQ ID NO: 12) and thrombocidin-2 (TC-2) (SEQ ID NO: 6) or variants thereof, such as TC-1*, (SEQ ID NO: 3), which comprise, at least in part, the sequence as shown in FIG. 1 and have broad antimicrobial activity. These peptides, or variants thereof, thus may be effectively used as antibiotics in the treatment of several infectious diseases. These peptides can be isolated from both human and animal tissue.

"Variants" of isolated or recombinant peptides TC-1 and TC-2 are peptides that are at least 70% homologous, preferably at least 80%, more preferably at least 90%, most preferably at least 95%, to TC-1 and TC-2 and also have antimicrobial activity in vitro, such as TC-1*.

It has been found that human and animal blood platelets contain factors that exhibit antibacterial and antifungal activity in vitro. Upon thrombin-activation platelets are known to release lysozyme, as well as a number of other cationic peptides. A number of these platelet-derived peptides have been identified, such as platelet factor-4 (PF-4), RANTES, connective tissue activating peptide (CTAP-III), platelet basic protein (PBP), and neutrophil activating peptide (NAP-2).

In the research that led to the invention, new peptides have been isolated from platelet granules, and have been purified and characterized. These peptides are small and strongly positively charged proteins and are named thrombocidins (TC). The positive charge of thrombocidins presumably accounts for their antibacterial activity. Thus, like other cationic antibacterial proteins, thrombocidins most likely form pores in bacterial membranes, as a result of which these bacteria will die. Since thrombocidins act on the bacterial membrane itself which can not easily be modified, resistance will not rapidly occur.

Thrombocidins are stored in alpha-granules of platelets and are released following thrombin-activation. The most active thrombocidins, TC-1 and TC-2 and variants, such as TC-1*, have been isolated, purified and characterized as described in further detail in the following examples. In short, thrombocidins were isolated from a large batch of human platelets. The first step was to isolate the platelet granules in which the thrombocidins are present. These platelet granules subsequently were disrupted and the protein content was collected for further purification. The thrombocidins were separated from other proteins on the basis of molecular size, polarity and charge.

The new peptides of the invention appear to be derivatives of NAP-2 and CTAP-III. NAP-2 itself is a N-terminal cleavage product of CTAP-III. TC-1 has been shown to be a mixture of C-terminal truncation products of NAP-2, of which the 7436 Da peptide, lacking two C-terminal amino acids, is the main component (referred to as variant TC-1*; (SEQ ID NO: 3) FIG. 1, table 1). A form of NAP-2 with an additional N-terminal tyrosine was also present as a minor component. TC-2 (SEQ ID NO: 2) has been identified as a C-terminal truncation product of CTAP-III (SEQ ID NO: 1) lacking the last two C-terminal amino acids, with a molecular weight of 9100 (FIG. 1A, table 1). Thrombocidins identified thus far are indicated in FIG. 1A, together with the known sequences of CTAP-III (SEQ ID NO: 1) and NAP-2 (SEQ ID NO: 13) (FIG. 1).

Figure 13:
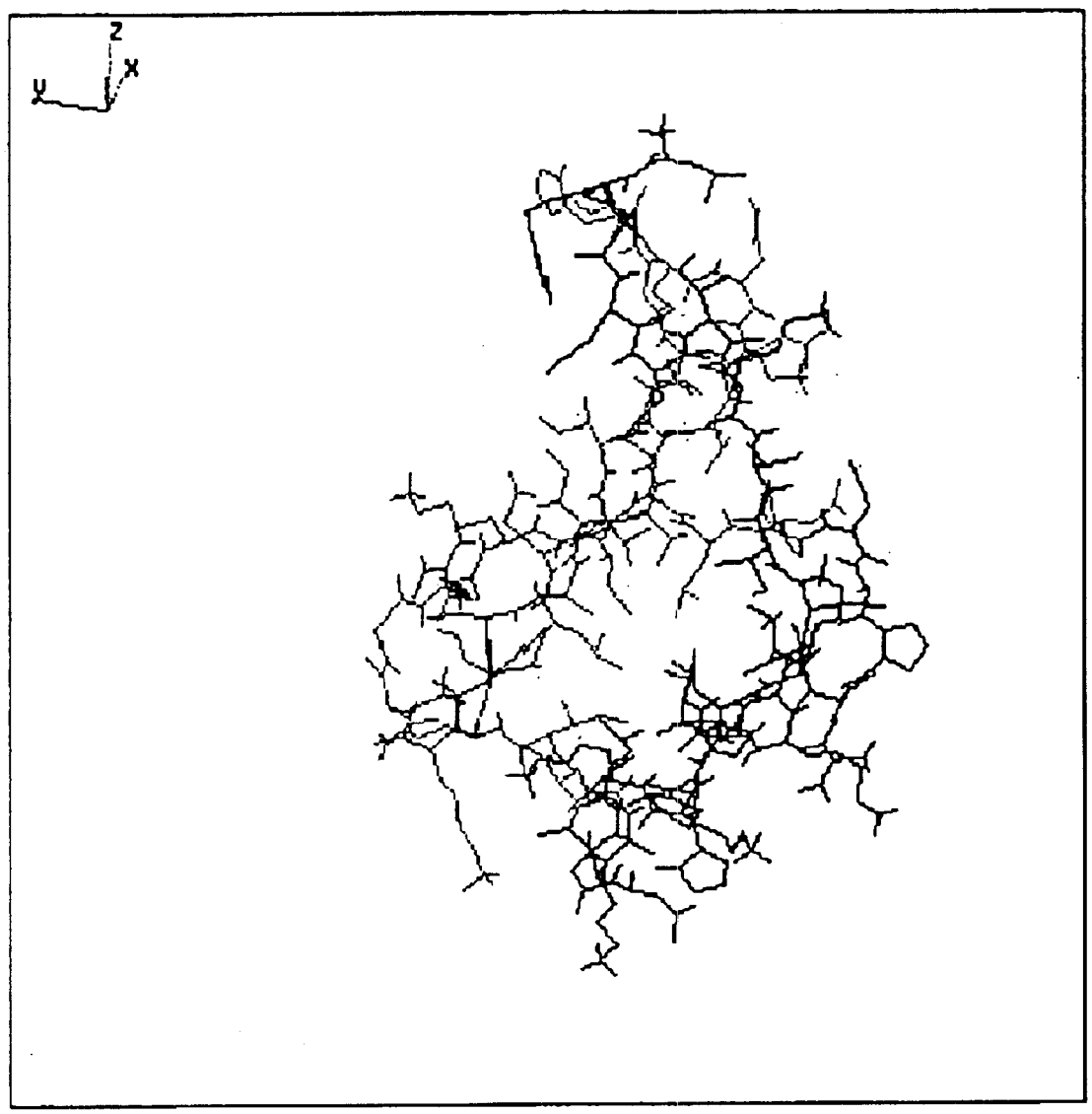

As described earlier, the thrombocidins are C-terminal truncation products of NAP-2 and CTAP-III, both of which are chemokines of the CXC family. These chemokines have a specific arrangement and disulfide-linkage of 4 cystein residues, giving the molecule a characteristic three dimensional structure (FIG. 13). Therefore it is well possible that other chemokines or chemokine-like molecules possess antimicrobial activity like the thrombocidins.

Based on the amino acid sequence of the native proteins the DNA coding for TC-1, NAP-2 and CTAP-III were now cloned and used to recombinantly produce these proteins in order to obtain larger quantities. Hereto, coding DNA was amplified from a human bone marrow cDNA library by PCR and cloned into a NdeI/BamHI digested pET9a or pET16b expression vector. Constructs were transformed to *E. coli* BL21DE3LysS cells and gene expression was induced by adding IPTG to growing cultures. Bacteria were harvested, lysed in guanidine, and recombinant proteins were purified to homogeneity in a two-step purification. Sequences of the purified recombinant proteins are shown in FIG. 2. Recombinant thrombocidins were also produced in the milk of animals.

Several classes of antibacterial proteins contain disulfide bonds. As far as it has been investigated, the presence of these disulfide bonds has been found to be essential for antibacterial activity of HNP-2 (Selsted and Harwig, 1989), GNCPs (Yomogida et al, 1995) and beneficial for activity of protegrins (Harwig et al, 1996). Because disulfide formation is critical for antibacterial activity, a prokaryotic system is not an obvious way to produce these proteins recombinantly. HNP has been produced recombinantly in *E. coli*, but indeed this product had no antibacterial activity, probably due to misfolding of the protein (Piers et al, 1993). Chemokines like NAP-2, CTAP-III (Proudfoot et al, 1997) and IL-8 (Lindley et al, 1988) have been produced in *E. coli*, but these proteins had to be refolded after they had been purified, a procedure which was not needed to observe antibacterial activity of the recombinant thrombocidins.

Bactericidal activity of TC-1* and TC-2 has been confirmed against a number of gram-positive, such as *Streptococcus sanguis, Staphylococcus aureus, Staphylococcus epidermidis*, and *Bacillus subtilis* and gram-negative bacteria such as *Escherichia coli*, which are found in a wide variety of infections.

One example of an infection in which the peptides of the invention may be used is endocarditis. Endocarditis is a serious infectious heart disease with high morbidity and mortality, associated with abnormalities of the heart endothelium or the heart valves. Lesions due to these abnormalities give rise to platelet adherence and activation. Together with other blood proteins, these platelets form a dense meshwork covering the lesion, to which bacteria that have entered the blood stream will adhere. In turn, more platelets will adhere to the bacteria and the 'clot' will grow, ultimately causing malfunctioning of the valve resulting in the need for valve replacement. *S. sanguis* is one of the microorganism prevalent in native valve endocarditis. Other bacterial, or fungal microorganisms may, however, also be found.

In the platelet clot, bacteria are protected from phagocytic cells, which cannot penetrate the dense platelet meshwork. In contrast, platelet-derived thrombocidins are capable of penetrating the clot and thus may effectively prevent bacterial proliferation.

Fungi against which the peptides of the invention may be effective comprise, for example: *Candida albicans, C. glabrata, Cryptococcus neoformans, Aspergillus flavus, A. fumigatus*, and *Pseudoallescheria* spec.

The present invention thus provides new, isolated or recombinantly prepared peptides TC-1 (SEQ ID NO: 12) and TC-2 (SEQ ID NO: 6), or variants thereof, such as TC-1* (SEQ ID NO: 3) (FIGS. 1 and 2), which exhibit antibacterial and/or antifungal activity and can be used in the treatment of infections in humans and animals. Furthermore, the peptides, or variants thereof, of the present invention can be used for the preparation of a medicament for the treatment of bacterial and/or fungal infections.

The invention is further illustrated, but not limited by the following examples and figures.

EXAMPLES

Example 1

Isolation Purification and Characterization of TC-1 and TC-2

A. Isolation of Granule Protein from Thrombocytes

Buffy coats of human blood from healthy subjects were obtained from the Central Laboratory for Bloodtransfusion, Amsterdam, The Netherlands. Eight buffy coats were pooled in a transfer bag (NPBI, Emmer-Compascuum, The Netherlands) (ca. 550 ml), and 200 ml of PBS+0.38% tri-sodium citrate (w/v) was added. The bag was blown tight with air and centrifuged for 5 min at 600 g and 20° C. The upper phase, containing mainly platelets, was transferred to a new transfer bag. To this platelet concentrate, ⅛ volume of citrate solution was added (75 mM trisodium citrate; 38 mM citric acid). The bag was blown tight again, and was centrifuged for 10 min at 1750 g (20° C.) to pellet platelets. Platelets were resuspended in the same bag in Tris-citrate (63 mM Tris-HCl; 95 mM NaCl; 5 mM KCl; 5 mM EDTA; pH 6.8) by gentle massage, and kept shaking overnight at 22° C. Then, platelets were collected in a siliconized flask and the transfer bag was washed with Tris-citrate. Processing of 48 buffy coats routinely yielded ca. 75 ml of highly concentrated platelet suspension containing <0.05% residual leukocytes.

To isolate platelet granules, the platelet concentrate was cavitated three times under nitrogen at 60 atm in a Parr cavitation chamber, and cavitate was collected in siliconized 50 ml tubes (Falcon). This resulted in ca. 90% homogenization of the platelets as determined by Coulter counting. Intact platelets and platelet ghosts were removed by centrifuging the cavitate at 5000 g for 20 min. The supernatant was collected and centrifuged at 12000 g for 20 min, yielding the granules in the pellet. The pellet was resuspended in 5% acetic acid, and sonicated for 30 seconds (pulsed) on ice to rupture granules. The sonicate was kept at 4° C. for 24 hours, and subsequently was centrifuged at 125000 g. The supernatant containing granule protein was dialyzed against 5% acetic acid.

B. Purification of Thrombocidin-1 and -2

A rapid two-step purification protocol was developed for the purification of TC-1 and TC-2 from platelet granule protein: i) cation exchange chromatography, and ii) preparative acid urea polyacrylamide gel chromatography (AU-PAGE), to yield highly purified protein preparations.

i) Cation Exchange Chromatography

As an ion exchange matrix, CM-sepharose 25 (Pharmacia) was used; phosphate buffer (50 mM, pH 7.0) was used as the mobile phase. A 25 ml sample, containing 3.5 mg/ml of granule protein from approximately 40 buffy coats, was loaded at 0.8 ml/min. Subsequently, the column was washed with phosphate buffer, and protein was eluted with a salt gradient from 0 to 1 M NaCl. Fractions were collected, dialyzed and assayed for the presence of antibacterial proteins by running two separate acid urea gels in parallel. One gel was silverstained (FIG. 3), the other gel was used in an overlay assay to detect antibacterial activity (FIG. 4). *E. coli* ML35 was used as the test organism. Selected fractions were analyzed by tricine gel electrophoresis to estimate molecular weights of the (partially) purified protein (FIG. 5). The activity present in the starting material (FIG. 3, cav) is eluted in fractions 35 through 75. Major antibacterial activity can be assigned to two proteins, the most cationic protein is designated as thrombocidin-1 (TC-1), the slightly less cationic as thrombocidin-2 (TC-2). These proteins migrate in an SDS gel as proteins with an apparent molecular weight of 5.5 and 6.5 kD, respectively (FIG. 5).

ii) Continuous AU-PAGE

Figure 6A:
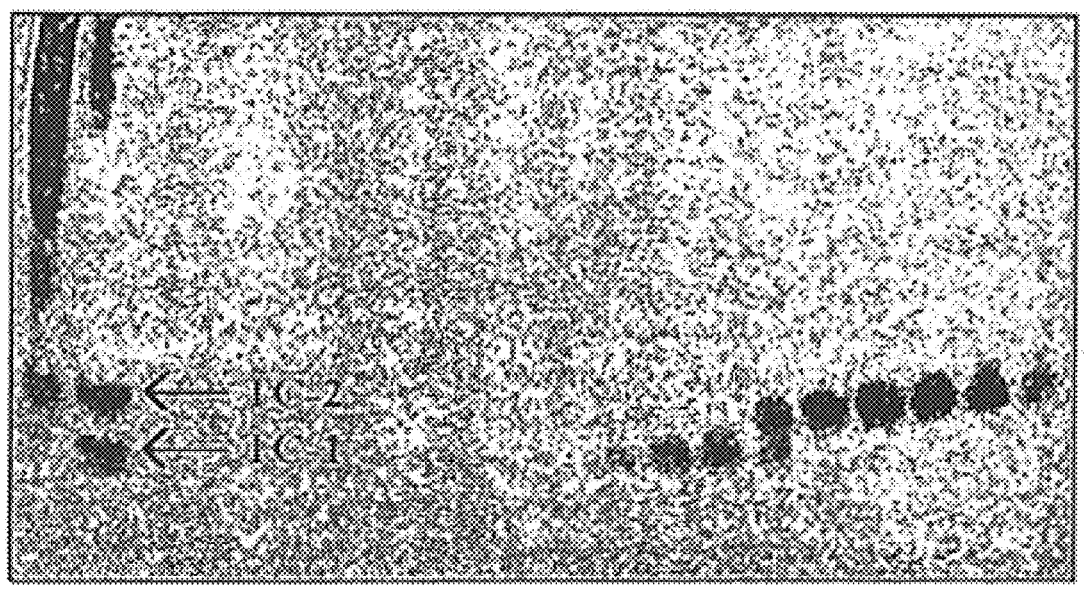
Figure 6B:
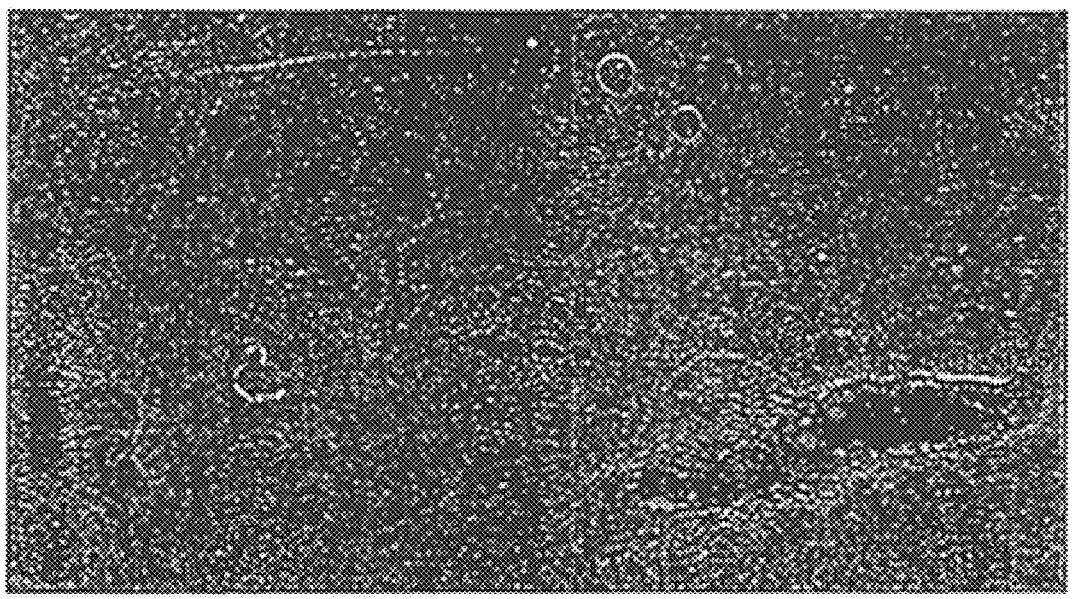

Fractions eluted from the CM-sepharose column containing antibacterial protein (30 through 75) were pooled, lyophilized, and subjected to a second purification step utilizing continuous gel electrophoresis. Cylindrical gels (3, 7×6 cm, 12.5% acrylamide, 3M urea, 5% acetic acid) were poured in a model 491 Prep Cell (BioRad, Veenendaal, The Netherlands) and polymerized at 37° C. Prerunning was at 200V for 2 h. Sample (max. 450 μl) was electrophorized at 40 mA. Protein was eluted in 5% acetic acid at 1 ml/min and collected in 5 ml fractions. Again, fractions were analyzed in two urea gels run in parallel, followed by staining or by an assay for antibacterial activity (FIG. 6). TC-1 and TC-2 could effectively be separated (FIG. 6*a*). Both proteins had considerable activity against *E. coli* ML35 (FIG. 6*b*). Purified TC-1 and TC-2 were lyophilized and redissolved in 0, 01% acetic acid, and stored at −20° C. until further analysis.

C. Structure of Thrombocidin-1 and -2

Figure 7A:
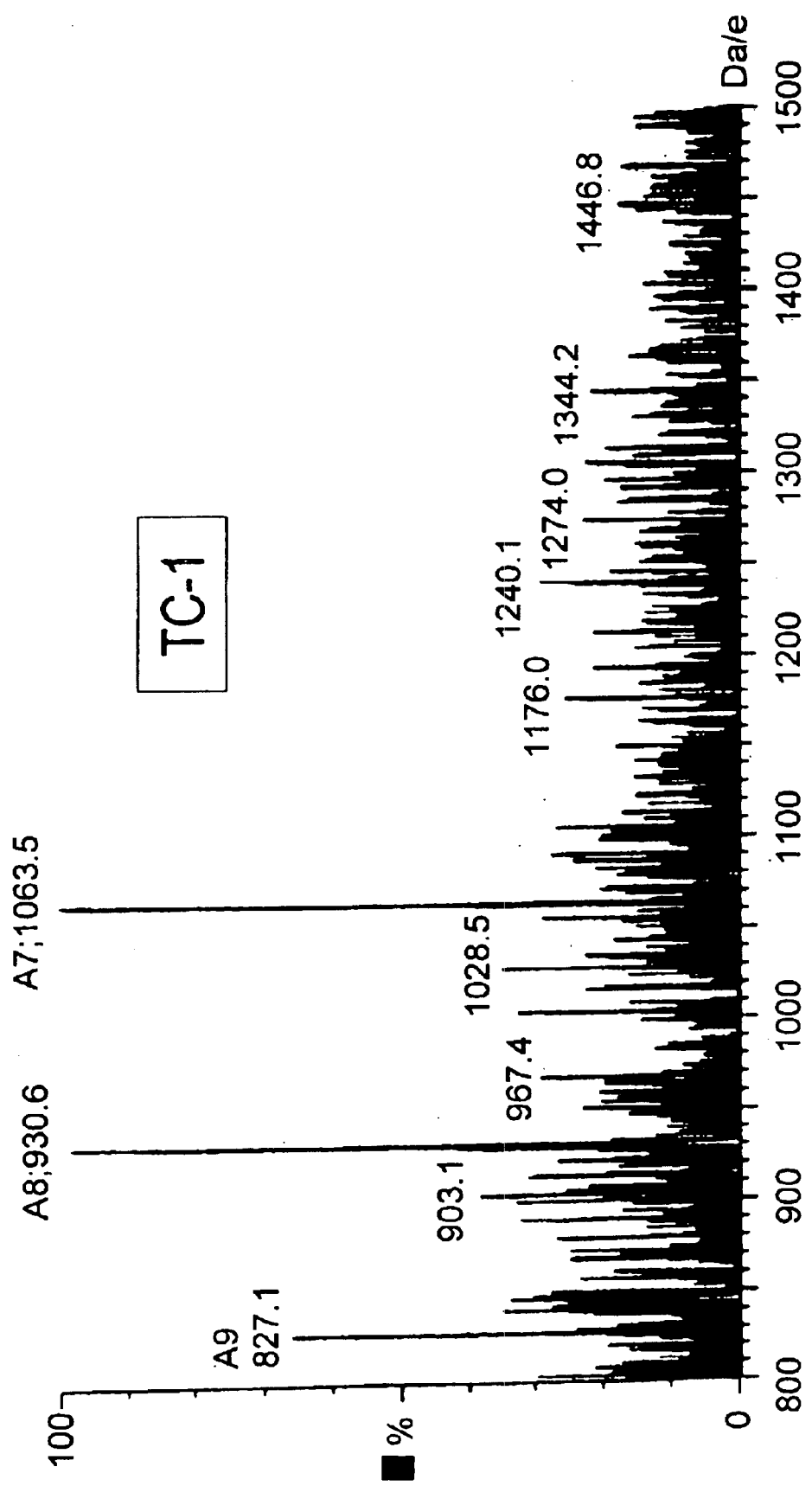

Bactericidal proteins thrombocidin-1 and -2, purified from human blood platelets, were analyzed by MALDI and electrospray (ES) mass spectrometry. ES analysis of TC-1 (FIG. 7*a*) yielded a molecular weight of 7436, 3±1,3 Da. Analysis by MALDI (FIG. 8) also revealed a peak of this size, next to an additional number of peaks with M+1 of 7107.2, 7227.7 and 7602,0 Da. The molecular weights of these proteins can be explained by assuming that these proteins are C-terminal truncation products of NAP-2; the calculated molecular weights correspond well with the values experimentally determined (Table 1). These data suggest that TC-1 is a mixture of C-terminally truncated forms of NAP-2. The 7436 Da protein seems to be the main component. We designated this protein TC-1*.

Figure 7B:
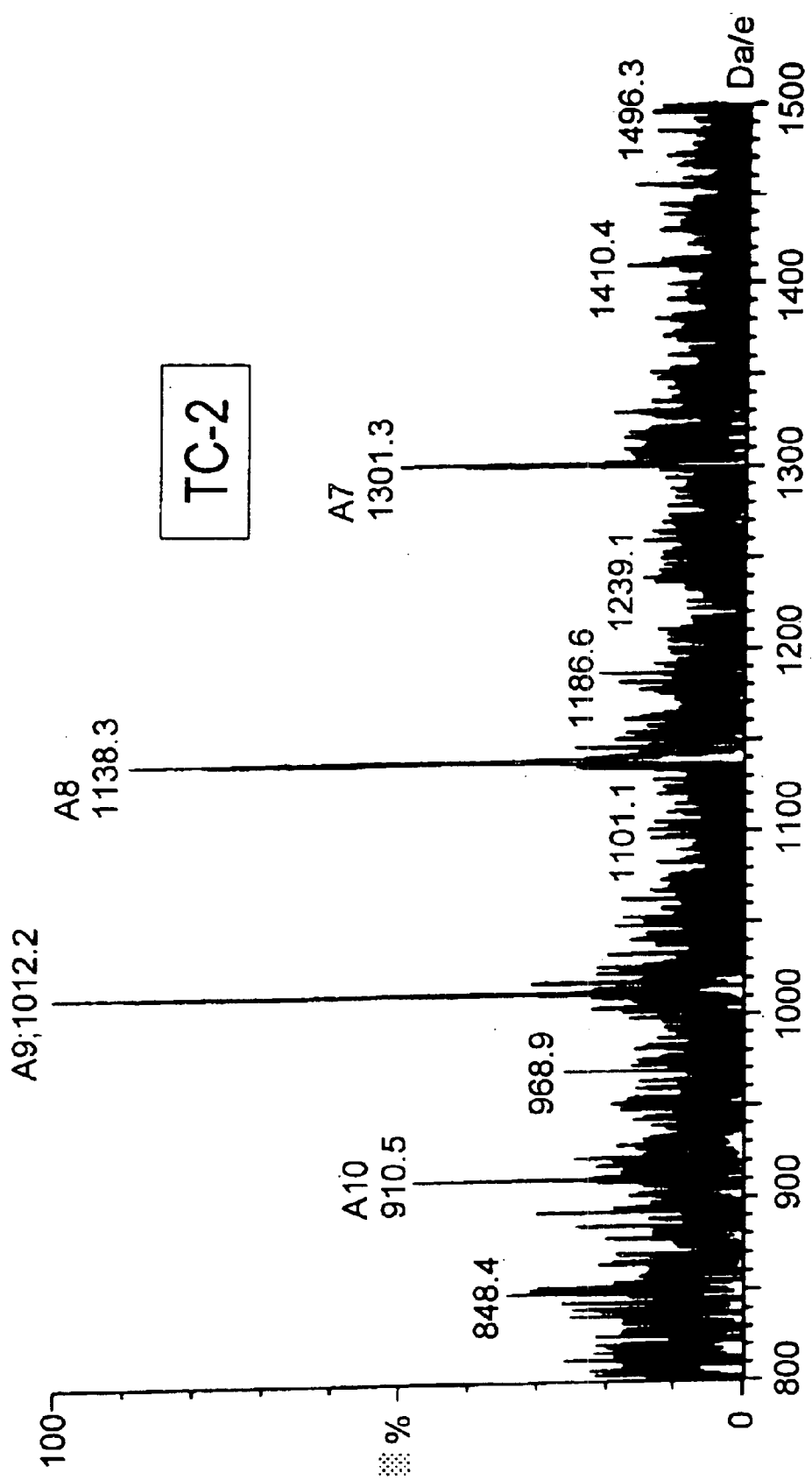

ES spectroscopy of TC-2 (FIG. 7b) yielded a molecular weight of 9100,5±1,3. This value was confirmed by MALDI-tof spectroscopy. In addition to TC-2, only one minor contamination was present (10081 Da, FIG. 9). Partial sequencing of TC-2 indicated that the N-terminus of TC-2 is identical to that of CTAP-III. Based on the mass-spectrometrical data (FIGS. 7b and 9) however, it appears that the mass found experimentally was smaller than the mass of CTAP-III (table 1). This can be explained by assuming that TC-2 is truncated C-terminally and misses 2 amino acids compared to CTAP-III. Thrombocidins identified thus far are indicated in FIG. 1, together with the sequences of CTAP-III (SEQ ID NO: 1) and NAP-2 (SEQ ID NO: 13).

5'GTGTAA<u>CATATG</u>AACTTGGCGAAAGGC
   AAAGAG-3' (SEQ ID NO: 9);

for NAP-2 and TC-1*;

5'GTGTAA<u>CATATG</u>TATGCTGAACTCCGCT
   GCATG 3' (SEQ ID NO: 10);

and for TC-1:

5'GTGTAA<u>CATATG</u>TATCTCCGCTGCATGT
   GTATAAAG-3' (SEQ ID NO: 11).

NdeI restriction sites (underlined) were included to allow cloning into the vectors. The PCR products were digested with NdeI/BamHI and ligated into a pET9a (TC-2, CTAP-III and TC-1*) or a pET16b vector (NAP-2 and TC-1), linearized with NdeI and BamHI. The recombinant proteins produced using the pET9a vector carry an additional N-terminal methionine, and are therefore designated as rMTC-1* and rMTC-2 and rMCTAP. The recombinant proteins produced using the pET16 vector carry an N-terminal His-tag, plus a tyrosine (Y) residue, and therefore designated as rYTC-1 and rYNAP. Constructs were transformed to E. coli DH5α, and plated on LB/kanamycin

TABLE 1

Interpretation of mass-spectrometrical data of TC-1 and TC-2: comparison with CTAP III

| Component | Mol. weight (Da) | | Sequence of | |
| --- | --- | --- | --- | --- |
| | MALDI/ES | Calc | N-terminus | C-terminus |
| CTAP-III | | 9287.2 | NLAKGKEESLDSDLYAELR (SEQ ID NO: 1) | ... AGDESAD |
| TC-1a | 7106.2 | 7105.8 | AELR (SEQ ID NO: 2) | ... AG |
| TC-1b | 7226.7 | 7220.9 | AELR (SEQ ID NO: 2) | ... AGD |
| TC-1* | 7436.3 | 7437.5 | AELR (SEQ ID NO: 3) | ... AGDES |
| TC-1d | 7601.0 | 7600.7 | YAELR (SEQ ID NO: 4) | ... AGDES (SEQ ID NO: 5) |
| TC-2 | 9100.5 | 9101.6 | NLAKGKEESLDSDLYAELR (SEQ ID NO: 6) | ... AGDES |

Example 2
Production of Recombinant (r) CTAP-III, rNAP-2, rTC-1, rTC-1* and rTC-2.

From a human bone marrow CDNA library (Clontech, Palo Alto, USA) DNA coding for PBP was amplified in a PCR. 5'TATA GGATCCATGAGCCTCAGACTTGATACCACC-3' (SEQ ID NO: 7) and 5' TATA GGATCCTCAATCAGCAGATTCATCACCTGCCAAT-3' (SEQ ID NO: 8) were used as forward and reverse primers, respectively. BamHI restriction sites (underlined) were added to allow cloning in a suitable vector. A stop sequence (boldface) was included to allow proper transcription termination at the stage of protein expression. This PCR was performed using 2 ng of template DNA and Pfu DNA polymerase, which has proofreading capacity. The resulting product was of the expected size (400 bp). This product served as a template in a second PCR to produce the coding DNA of TC-1 (SEQ ID NO: 12), TC-2, CTAP-III (SEQ ID NO: 1), NAP-2 (SEQ ID NO: 13) and TC-1* (SEQ ID NO: 3), a variant of TC-1 which lacks two C-terminal amino acids (Ala-Asp) and carries two additional N-terminal amino acids (Ala-Glu) (FIG. 2). These PCR products were cloned into expression vectors. For CTAP-III, NAP-2 and TC-1 the reverse primer was the same as the reverse primer described above. The forward primers were as follows: for CTAP-III and TC-2:

(50 μg/ml) (pET9a) or LB/ampicillin (50 μg ml) (pET16b) plates. Sequencing of cloned DNA confirmed the correct sequence in the constructs. Plasmids containing the correct insert were isolated and transformed to BL21(DE3)lysE cells, and plated on LB plates supplemented with the proper antibiotics. Of each plate, single colonies were picked, grown and stored in glycerol broth at 70° C. until further use. Cultures of BL21(lysE) cells transformed with the CTAP-III, NAP-2 TC-1 or TC-1* genes containing pET expression vector were grown in LB medium supplemented with the proper antibiotics. Growing cultures with $OD_{660}$ of 0.3 were induced with IPTG (1 mM final concentration). After 3 hours of induction, cells were harvested by centrifugation (5 min, 5000 g) and lysed in 20 mM Tris HCl, pH 8,2 containing 6M guanidine HCl. Cell debris was removed by centrifugation. Supernatants of rMCTAP and r-MTC producing cells were dialyzed against 50 mM phosphate buffer, pH 7,0.

rMTC-1*, rMTC-2 and rMCTAP were purified by CM-sepharose cationexchange chromatography and continuous acid urea gel electrophoresis, as described for TC-1* and TC-2 in example 1. The N-terminal His-tag in rYTC-1 and rYNAP allowed purification of these proteins using a His binding resin (Novagen). Final purification was performed by continuous AU PAGE. The structures of the purified recombinant proteins were confirmed by MALDI and ES mass-spectrometry.

Example 3
Antibacterial Activity

The experimental set-up for testing antibacterial activity of thrombocidins was as follows. Bacteria from blood agar plates were grown overnight in tryptic soy broth (TSB), subcultured in fresh TSB and grown to log-phase in 2–3 hours. Bacteria were pelleted, washed once in 10 mM phosphate buffer (pH 7,0)+1% TSB (v/v) and resuspended in the same medium to an $OD_{620}$ of 0,1. This suspension was further diluted 200 (*B. subtilis*) or 500 times (*E. coli* and *S. aureus*) to obtain suspensions containing $0.5-1\times10^5$ colony forming units (cfu)/ml. In a polypropylene microtiter plate a serial dilution series of the protein to be tested was prepared in 0,01% acetic acid. To 5 μl of every sample, 45 μl of bacterial suspension ($0.5-1\times10^5$ cfu/ml) was added. The plate was incubated on a rotary shaker (400 rpm) at 37° C. After 2 hours, 0,5 and 10 μl samples were plated on blood agar plates. Bactericidal activity was calculated the next day after colony counting. All experiments were performed in duplicate.

Bactericidal activity of TC-1* and TC-2 was determined against *E. coli* ML35, *S. aureus* 42D and *B. subtilis* ATCC6633 in killing assays (FIG. 10).

In FIG. 10 it can be seen that TC-1* and TC-2 are bactericidal against a all three bacteria tested, and that TC-1* is the more active component.

Figure 11:
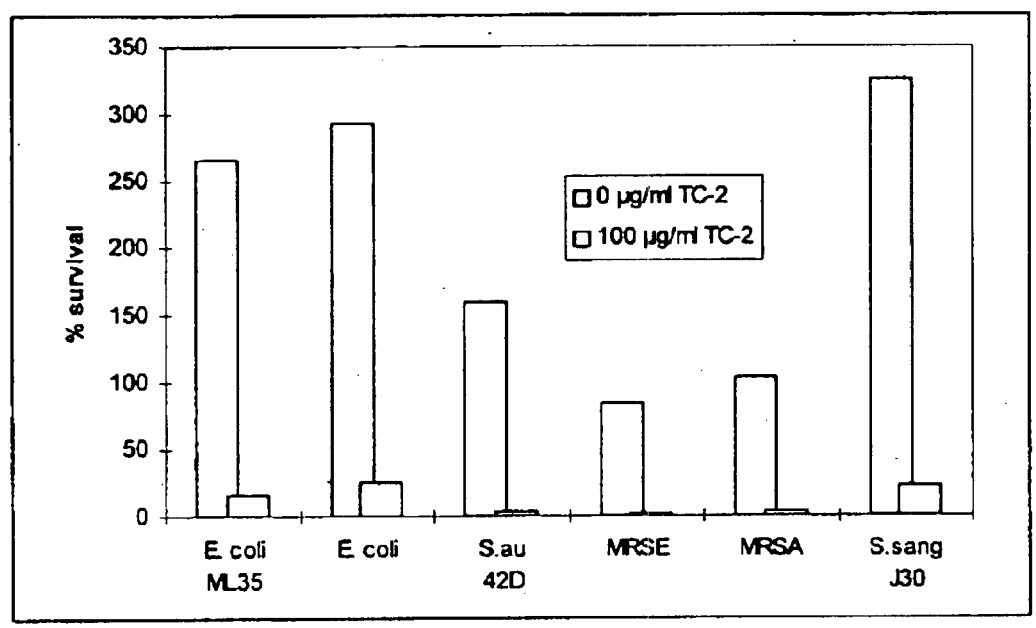

Bactericidal activity of TC-2 was tested against a panel of other bacterial species. The same method was used as described above, except that 5% Brain Heart Infusion (BHI) (v/v in water) instead of phosphate buffer+TSB was used as a test medium and one concentration of TC-2 was tested, being 100 μg/ml. Bacteria tested were *E. coli* ML35, wild-type *E. coli*, *S. aureus* 42D, multi-resistant *S. aureus* (MRSA), multiresistant *S. epidermis* (MRSE), and *S. sanguis* J30 (FIG. 11). The MRSA and MRSE are as susceptible to TC-2 as *S. aureus* 42D, while. *S. sanguis* J30 seems to be slightly less susceptible.

Analysis of TC-1 and TC-2 in a non-reducing tricine gel revealed that the migration of both peptides was retarded compared to their reduced forms. This indicated that TC-1 and TC-2 contain disulfide bridges. To investigate whether the disruption of these disulfide bridges influenced antibacterial activity, reduced TC-2, reduced and alkylated TC-2, and non-reduced TC-2 were analysed for antibacterial activity using an acid urea gel overlay system. All three forms of TC-2 were equally active (FIG. 12), indicating that disulfide bridges are not needed for TC-2 antibacterial activity. TC-1 was treated in the same way and showed similar results.

In general, disulfide bonds of cationic antibacterial proteins are considered to be essential for their antibacterial activity (Selsted and Harwig, 1989, Yomogida et al, 1995, Harwig et al, 1996, Piers et al, 1993, Proudfoot et al, 1997 and Lindley et al, 1988). The fact that in TC-1 and TC-2 the disulfide bonds are not needed for antibacterial activity is an unexpected finding.

MBCs of rMTC-1*, rMTC-2 and rMCTAP were determined for a number of organisms (Table 2). It appeared that rMTC-1* and rMTC-2 are bactericidal for *B. subtilis*, although MBCs are somewhat higher than for the native proteins (FIG. 10). The MSC of rMTC-1* for *E. coli* (3,8 μM) is the same as the MBC of the native protein TC-1* (FIG. 10), whereas the MBC of rMTC-1* for *S. aureus* (15 μM) is approximately 2-fold higher than for TC-1* (FIG. 10). In contrast to this, rMCTAP was not bactericidal for *E. coli*, *B. subtilis* and *S. aureus* at concentrations up to 40 μM. Recombinant NAP-2 (obtained from Bachem, Switzerland) was tested against *B. subtilis* up to 7 μM, but no killing was observed.

TABLE 2

MBCs (μM) of recombinant proteins for various bacteria.

|  | B. subtilis | E. coli | S. aureus |
|---|---|---|---|
| rMTC-1* | 3.8 | 3.8 | 15 |
| rMTC-2 | 7.5 | 15 | >15 |
| rMCTAP | >40 | >30 | >30 |
| rNAP-2 | >7 |  |  |

Bactericidal activity of rYTC-1 has been tested in a liquid assay as has been done for the native TCs. In comparison to the native thrombocidins TC-1* and TC-2, rYTC-1 is equally active against *B. subtilis*, but is more active against *S. aureus* 42D, and *E. coli* ML35 (table 3, FIG. 10). Additional experiments showed that rYTC-1 is highly active against a large number of bacterial species and against *Cryptococcus neoformans* (Table 3).

TABLE 3

Microbial activity of rYTC-1

| Organism | MBC (μM) of rYTC-1 |
|---|---|
| E. coli 69187 (EPEC) | 0.9 |
| E. coli 72540 (EPEC) | 0.4 |
| E. coli (genta 0) | 0.9 |
| E. coli ML35 | 0.9 |
| Pseudomonas aeruginosa | 3.8 |
| Neisseria meningitidis W135 | 1.9 |
| Klebsiella | 1.9 |
| Bacillus subtilis ATCC6633 | 0.4 |
| S. aureus 42 D | 1.9 |
| MRSA | 1.9 |
| S. Epidermis RP62 | 0.9 |
| S. Epidermis AMC 43 | 0.6 |
| S. Epidermis AMC 48 | 0.6 |
| S. Epidermis AMC 77 | 0.6 |
| S. Epidermis AMC 82 | 1.2 |
| S. Epidermis AMC 89 | 0.6 |
| MRSE | 1.2 |
| S. sanguis U108 | 1.9 |
| S. sanguis J30 | 1.9 |
| Cryptococcus neoformans | 0.4 |

Bactericidal activity of rMTC-1* against *S. aureus*, *E. coli*, and *B. subtilis* was significantly lower than that of rYTC-1 (table 2 and 3). The marked difference in bactericidal activity between rMTC-1* vs rNAP-2, and between rMTC-2 vs rMCTAP (Table 3) shows that the 2 additional C-terminal amino acids, alanin (A) and aspartic acid (D) present in rNAP-2 and rMCTAP strongly reduce bactericidal activity. Although these C-terminal amino acids are also present in rYTC-1, this protein is more active than rMTC-1*, which lacks the 2 C-terminal amino acids. In fact, rYTC-1 had more potent antibacterial activity than any of the native or recombinant proteins and rYTC-1 was also more active (MBC 0.4 μM) against *Cryptococcus neoformans* than rMTC-1* (MBC 7.5 μM) and rMTC-2 (MBC 15 μM). This indicates, that the N-terminal His-tag-containing sequence of rYTC-1 is involved in enhanced bactericidal activity, which has not been demonstrated before.

FIGURE LEGENDS

FIG. 1: Sequences of thrombocidins and elated proteins.

FIG. 2: Recombinant proteins produced. Boxes indicate antimicrobial activity enhancing sequence (Histag).

FIG. 3: Analysis of CM-sepharose purified platelet granular antibacterial protein. Selected fractions (as indicated) were run on AU-gels followed by silverstaining.

cav: crude granule extract (cavitate), starting material for the purification.

Figure 4:
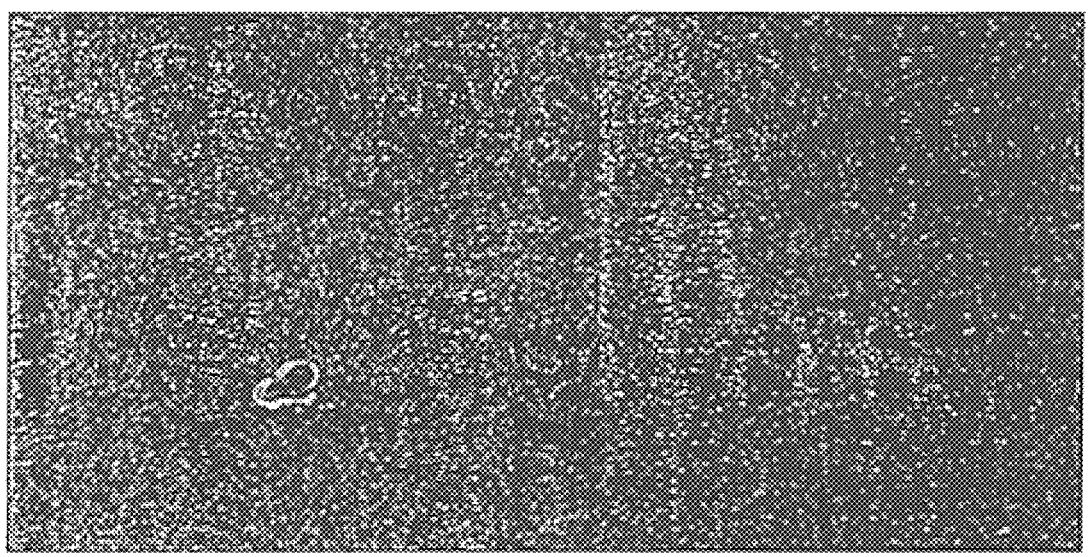
Figure 5:
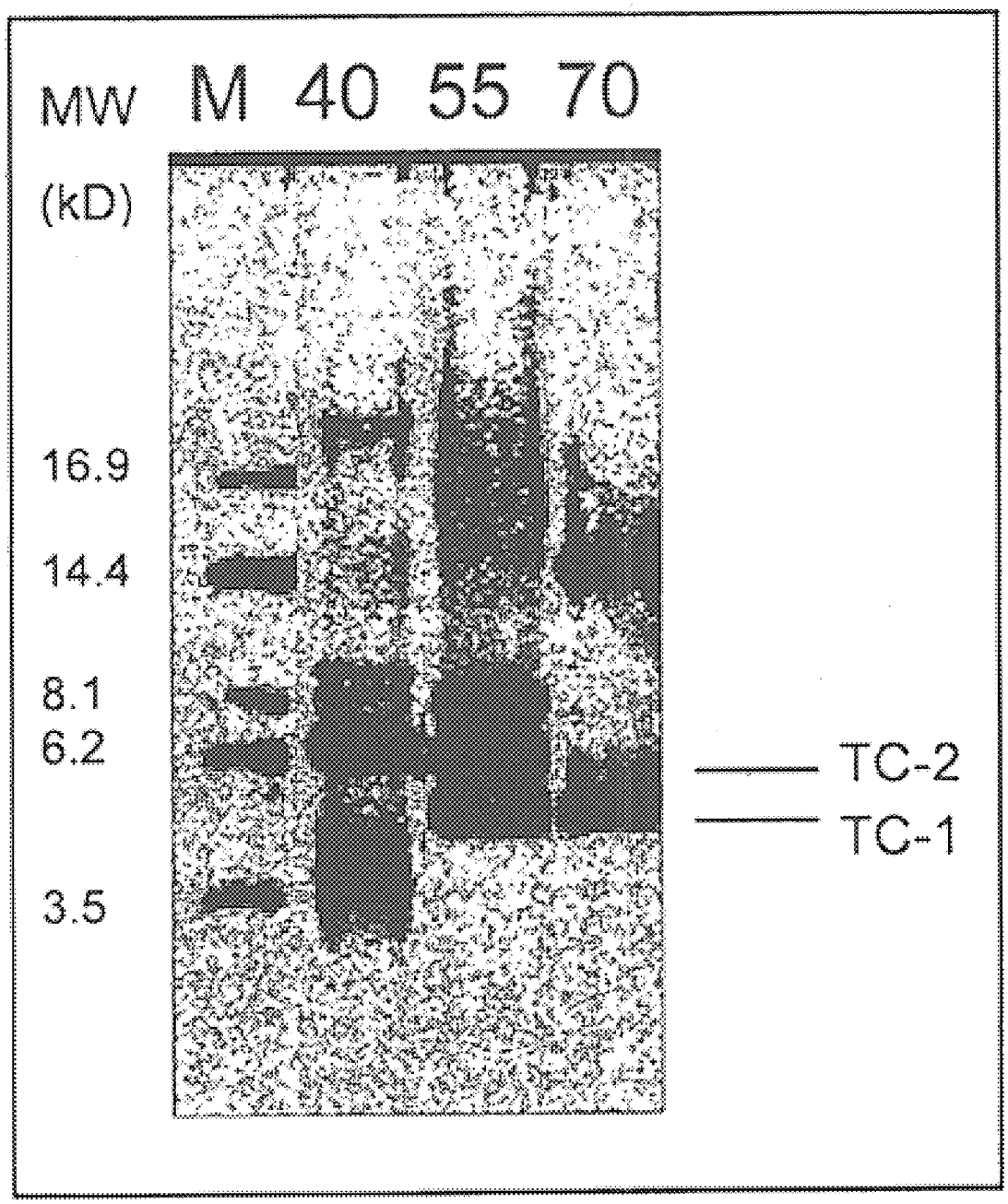

FIG. 4: Analysis of CM-sepharose purified platelet granular antibacterial protein. Selected fractions (as indicated) were run on AU-gels followed by an overlay using *E. coli* as a test organism.
cav: crude granular extract (cavitate), starting material for the purification.

FIG. 5: Analysis of CM-sepharose purified platelet granular protein by tricine SDS-electrophoresis. Silverstained gel. Selected fractions (compare FIG. 3) were anlayzed.

FIG. 6: Analysis of AU-PAGE purified platelet granular antibacterial protein. Selected fractions (as indicated) were run on AU-gels followed by silverstaining (A) or followed by an overlay using *E. coli* as a test organism (B).
cav: crude granular extract (cavitate); CM: pooled active fractions (30–75) eluted from a CM-sepharose column.

Figure 7C:
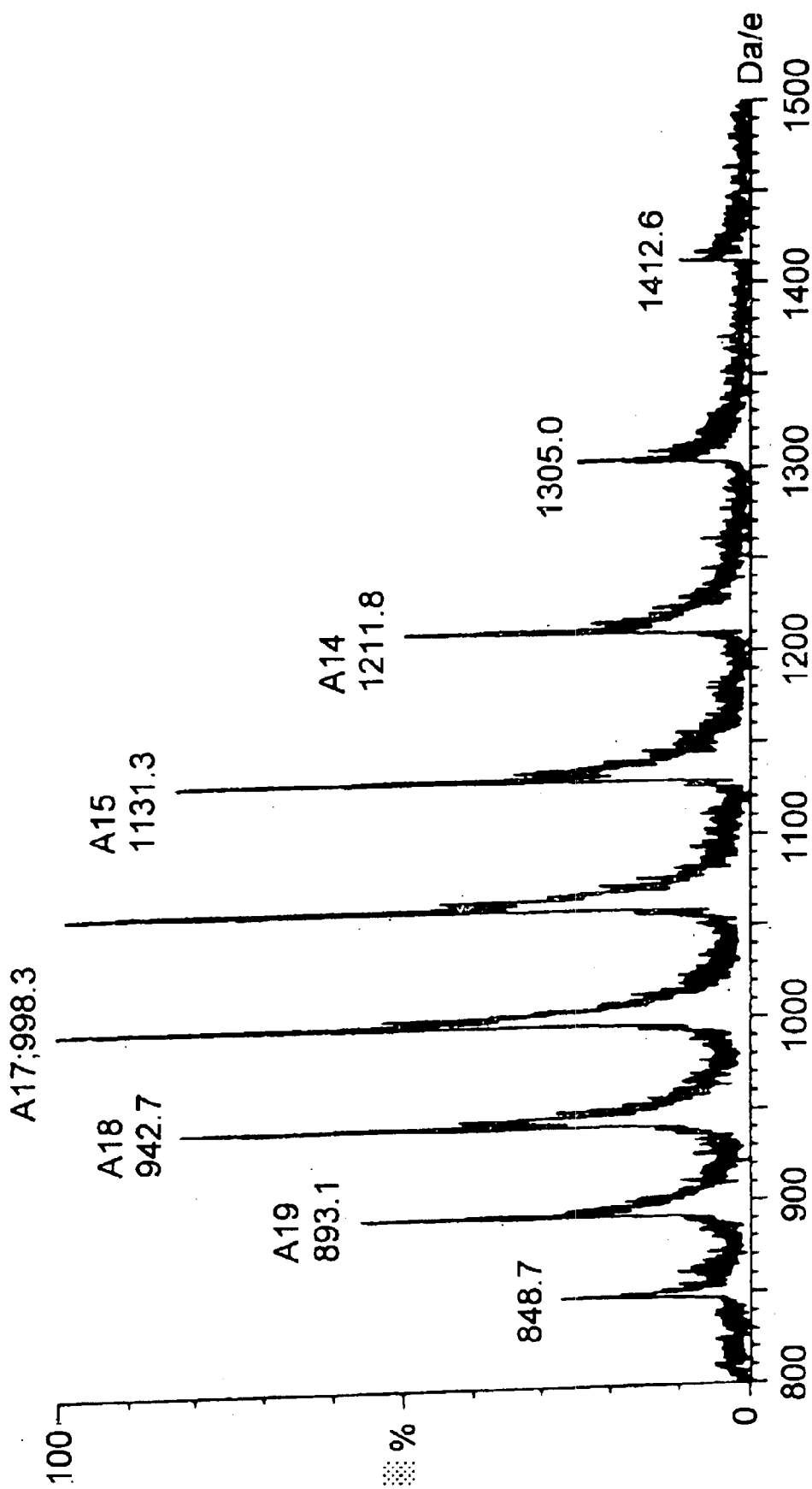

FIG. 7: Electrospray mass spectrometrical analyses of TC-1 (A) and TC-2 (B).

Figure 8:
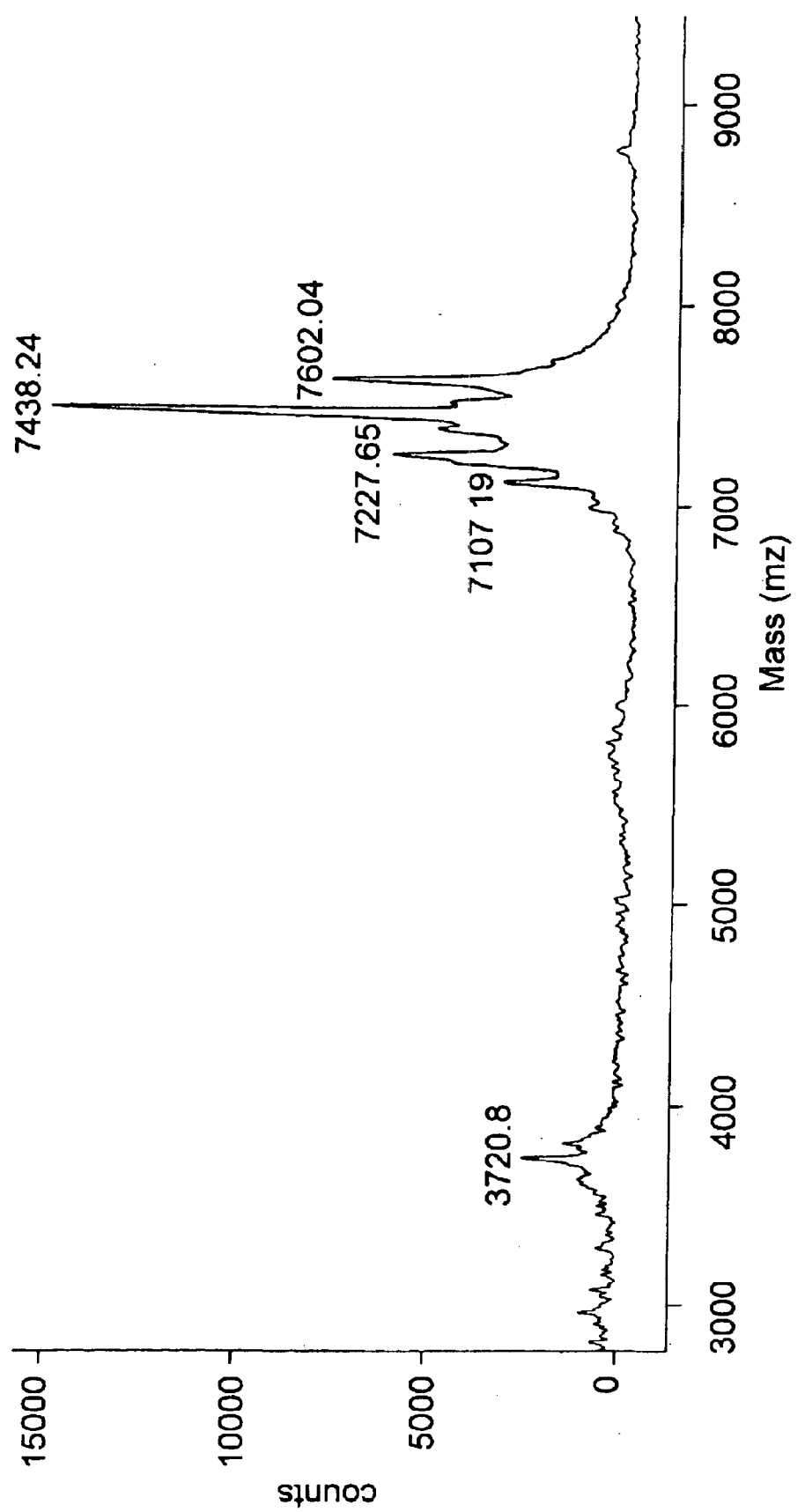

FIG. 8: MALDI-tof mass spectrometrical analysis of TC-1.

Figure 9:
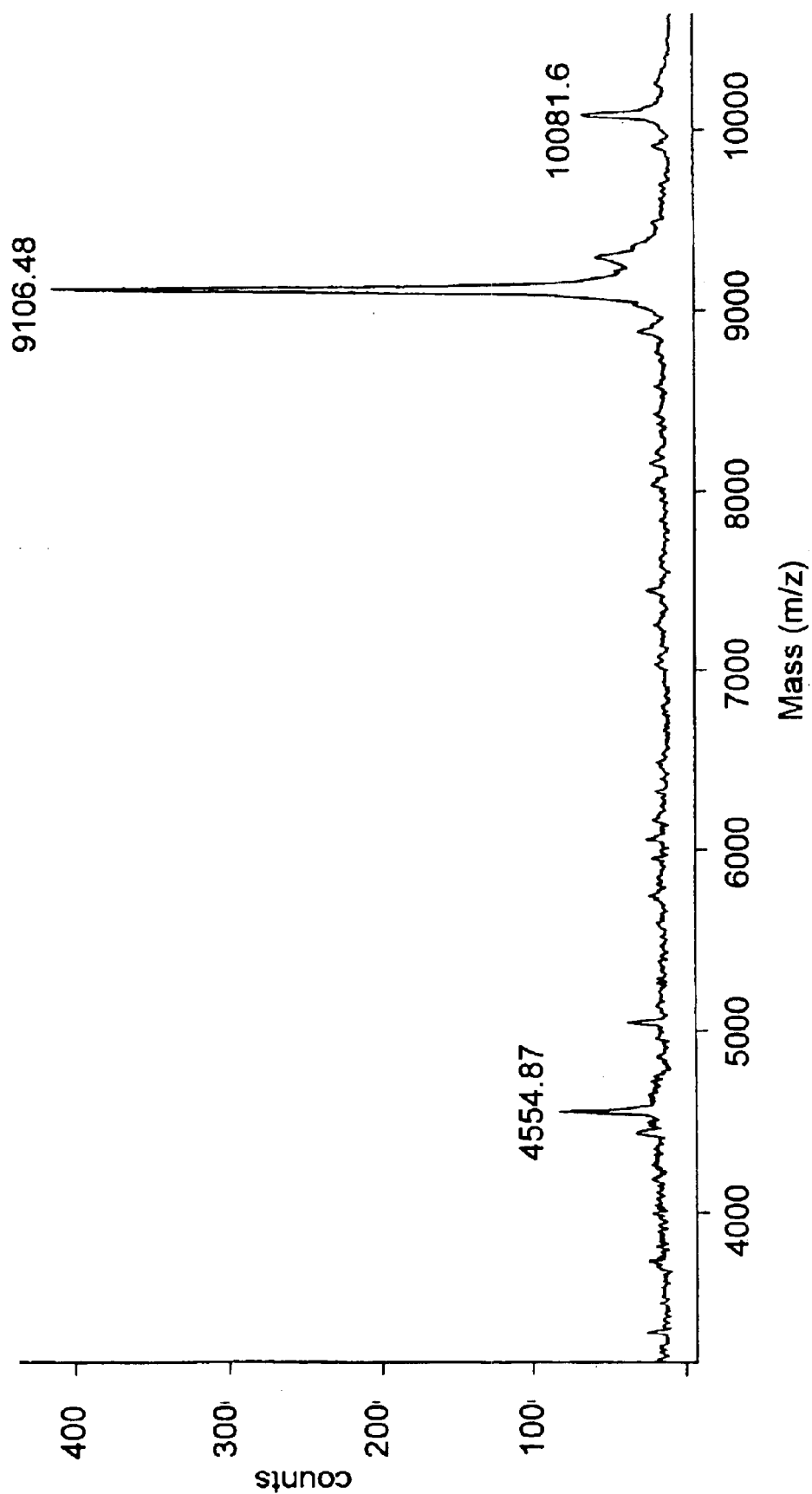

FIG. 9: MALDI-tof mass spectrometrical analysis of TC-2.

FIG. 10: Antibacterial activity of TC-1 (top panel) and TC-2 (bottom panel) against *E. coli* ML35, *S. aureus* 42D, and *B. subtilis* ATCC6633 (0,5–1×10$^5$ cfu/ml) were incubated in the presence of serially diluted TC (concentrations are indicated). After 2 hours of incubation bacteria were plated and survival was determined by colony counting. Medium: 10 mM phosphate buffer pH 7,0+1% TSB. Of TC-2 0,3 and 0,7 μM were not tested against *S. aureus* and *E. coli*.

FIG. 11: Killing of bacteria (1–2×10$^5$ cfu/ml) by TC-2 after 2 hrs incubation.

Figure 12:
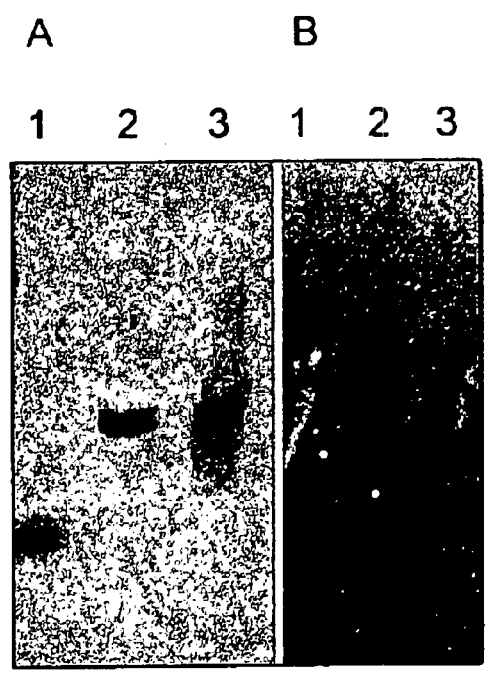

FIG. 12: Antibacterial activity of TC-2 and reduced TC-2. Panel A: silverstained acid urea gel. Panel B: Overlay of acid urea gel (test organism: *E. coli*). Lanes 1: TC-2; Lanes 2: reduced and carboxymethylated TC-2. Lanes 3: TC-2 reduced by β-mercaptoethanol treatment. Each lane contains approximately 3 μg of protein.

FIG. 13: Three-dimensional structure of CXC chemokines.

REFERENCES

Harwig, S S L, A Waring, H J Yang, Y Cho, L Tan, R I Lehrer (1996): Intramolecular disulfide bonds enhance the antimicrobial and lytic activities of protegrins at physiological sodium chloride concentrations. Eur J. Bioch 240: 352–357.

Lindley, I, H Aschauer, J Seifer, C Lam, W Brunowsky, E Kownatzki, M Thelen, P Peveri, B Dewald, V von Tscharner, A Walz, M Baggiolini (1988): Synthesis and expression in *Escherichia coli* of the gene encoding monocyte-derived neutrophil-activating factor: biological equivalence between natural and recombinant neutrophil-activating factor. Proc. Natl. Acad.Sci. USA 85: 9199–9203.

Piers, K L, M H Brown, R E W Hancock (1993): Recombinant DNA procedures for producing small antimicrobial cationic peptides in bacteria. Gene 137: 7–13.

Proudfoot, A E I, M C Peitsch, C A Power, B Allet, J Mermod, K Bacon and N C Wells (1997): Structure and bioactivity of recombinant human CTAP-III and NAP-2. J. Protein Sci. 16: 37–49.

Selsted, M E, and S S L Harwig (1989): Determination of the disulfide array in the human defensin HNP-2. A covalently cyclized peptide. J. Biol. Chem. 264: 4003–4007.

Yomogida S, I Nagaoka, T Yamashita (1995): Involvement of cysteine residues in the biological activity fragments of guinea pig neutrophil cationic peptides. Infect. Immun 63: 2344–2346.

What is claimed is:

1. Isolated microbicidal peptide which exhibits bactericidal and/or fungicidal activity having an amino acid sequence consisting essentially of the amino acid sequence of TC-1 as given in FIG. 1 (SEQ ID NO: 12), with modifications selected from the group consisting of: removing at least the two C-terminal amino acids alanine and aspartic acid and providing the peptide with an N-terminal His-tag-containing sequence.

2. Isolated peptide as claimed in claim 1, wherein the amino acid sequence of TC-1 is extended at its N-terminus with at least one of the following selections of amino acids, given from N-terminus to C-terminus:
   (a) the 17 N-terminal amino acids of TC-2 in the sequence as given in FIG. 1 (SEQ ID NO: 6) or fragments thereof; or
   (b) a methionine; or
   (c) a tyrosine; or
   (d) a methionine and the 17 N-terminal amino acids of TC-2 in the sequence as given in FIG. 1 (SEQ ID NO: 6) or fragments thereof; or
   (e) a methionine and a tyrosine; or
   (f) a methionine and a tyrosine and the 17 N-terminal amino acids of TC-2 in the sequence as given in FIG. 1 (SEQ ID NO: 6) or fragments thereof,
wherein, in the case in which a His-tag containing sequence is present, this sequence is located N-termninally of the peptides as defined in (e) or (f).

3. Isolated microbicidal peptide according to claim 1, wherein the peptide is thrombocidin-1 (TC-1) as depicted in FIG. 1 (SEQ ID NO:12).

4. Isolated microbicidal peptide according to claim 2, wherein the peptide is thrombocidin-2 (TC-2) as depicted in FIG. 1 (SEQ ID NO: 6).

5. Isolated microbicidal peptide according to claim 1, wherein said peptide exhibits bactericidal activity against at least one of *Escherichia coli, Bacillus subtilis, Streptococcus sanguis, Streptococcus pneumoniae, Staphylococcus epidermis*, and *Staphylococcus aureus*.

6. Isolated microbicidal peptide according to claim 1, wherein said peptide exhibits fungicidal activity against at least one of *Candida albicans, C. glabarata, Cryptococcus neoformans, Aspergillus flavus, A. fumigatus*, and *Pseudoallescheria* spec.

7. Method for the treatment of at least one of bacterial infection and fungal infection in humans and animals, comprising administering an isolated microbicidal peptide according to claim 1.

8. The method of claim 7, wherein the infection is endocarditis.

* * * * *